United States Patent
Kovács et al.

(10) Patent No.: US 10,338,043 B2
(45) Date of Patent: Jul. 2, 2019

(54) P-NITROPHENOLE-FORMALDEHYDE POLYCONDENSATE FOR MEASUREMENT, METHOD OF PRODUCTION AND USE

(71) Applicant: PÉCSI TUDOMÁNYEGYETEM, Pécs (HU)

(72) Inventors: Barna Kovács, Pécs (HU); Katalin Balogh, Somogyudvarhely (HU); Aleksandar Secenji, Pécs (HU)

(73) Assignee: Pécsi Tudományegyetem, Pécs (HU)

( * ) Notice: Subject to any disclaimer, the term of this patent is extended or adjusted under 35 U.S.C. 154(b) by 123 days.

(21) Appl. No.: 15/515,697

(22) PCT Filed: Sep. 29, 2015

(86) PCT No.: PCT/HU2015/050009
§ 371 (c)(1),
(2) Date: Mar. 30, 2017

(87) PCT Pub. No.: WO2016/051217
PCT Pub. Date: Apr. 7, 2016

(65) Prior Publication Data
US 2017/0307572 A1    Oct. 26, 2017

(30) Foreign Application Priority Data

Sep. 30, 2014  (HU) ..................... 1400460
Jun. 17, 2015  (HU) ..................... 1500285

(51) Int. Cl.
*G01N 31/22*  (2006.01)
*C08G 12/04*  (2006.01)
(Continued)

(52) U.S. Cl.
CPC ........... *G01N 31/221* (2013.01); *C08G 12/04* (2013.01); *G01N 33/18* (2013.01); *G01N 33/48* (2013.01)

(58) Field of Classification Search
None
See application file for complete search history.

(56) References Cited

U.S. PATENT DOCUMENTS 3,952,132 A  4/1976 Kato et al.
4,500,691 A  2/1985 Stockinger et al.
(Continued)

OTHER PUBLICATIONS

Godinho, O.E.S. et al. Formalin and Paraformaldehyde as End-point indicators in Catalytic Thermometric Titrimetry, Analyst, vol. 118, pp. 1453-1456 (Year: 1993).*
(Continued)

*Primary Examiner* — Xiaoyun R Xu
(74) *Attorney, Agent, or Firm* — Jason D. Voight

(57) ABSTRACT

The invention relates to a wide range optical sensor for measuring pH, wherein said optical sensor contains a carrier and one or more p-nitro-phenyl/formaldehyde condensed polymer of formula (I) bounded to said carrier wherein n is 1-20, and Z is H or binding group.

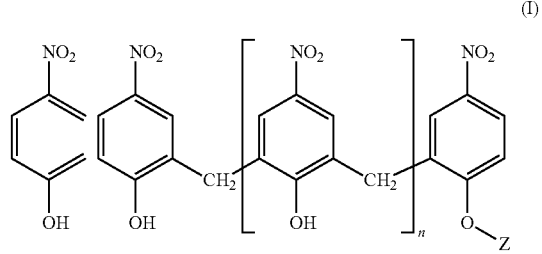

7 Claims, 3 Drawing Sheets

The normalized calibration curves of p-nitro-phenol (a), the PI-1 indicator (b) and the PI2 indicator (c) in a water-tetrahydrofurane mixture

(51) Int. Cl.
*G01N 33/18* (2006.01)
*G01N 33/48* (2006.01)

(56) References Cited

U.S. PATENT DOCUMENTS

| | | | |
|---|---|---|---|
| 5,017,452 A | | 5/1991 | Feldman |
| 5,039,492 A | | 8/1991 | Saaski et al. |
| 5,267,532 A | * | 12/1993 | Franklin .............. A01K 1/0152 |
| | | | 119/171 |
| 5,808,108 A | * | 9/1998 | Chappelow .......... A61K 6/0017 |
| | | | 106/35 |
| 2004/0241331 A1 | | 12/2004 | Durairaj et al. |
| 2009/0084175 A1 | | 4/2009 | Raghuraman et al. |
| 2012/0024224 A1 | * | 2/2012 | Kanchiku ................. B41C 1/05 |
| | | | 118/46 |

OTHER PUBLICATIONS

Kushwaha et al.: "Semiconducting behavior and anitbacterial activity of some resins derived from p-Nitrophenol, Resorcinol and Formaldehyde", Der Pharma Chemica, 2012, vol. 4(1), pp. 557-567.

\* cited by examiner

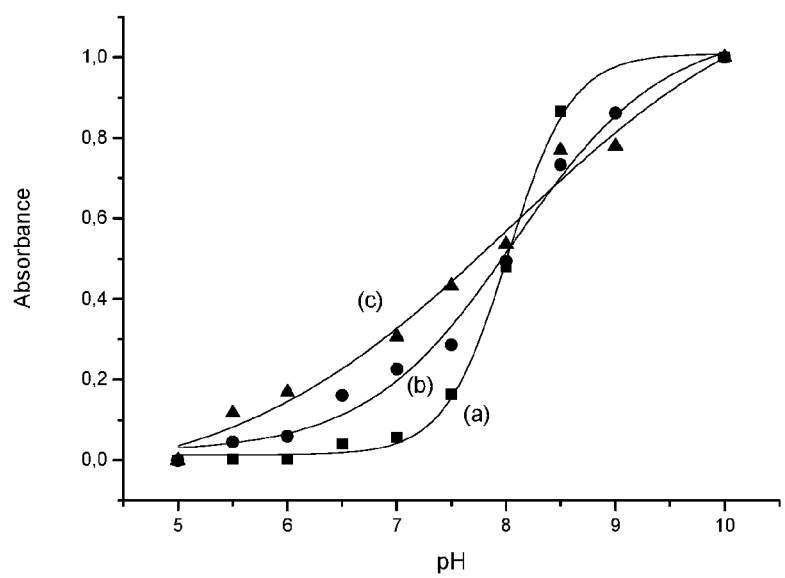
Figure 1: The normalized calibration curves of p-nitro-phenol (a), the PI-1 indicator (b) and the PI2 indicator (c) in a water-tetrahydrofurane mixture

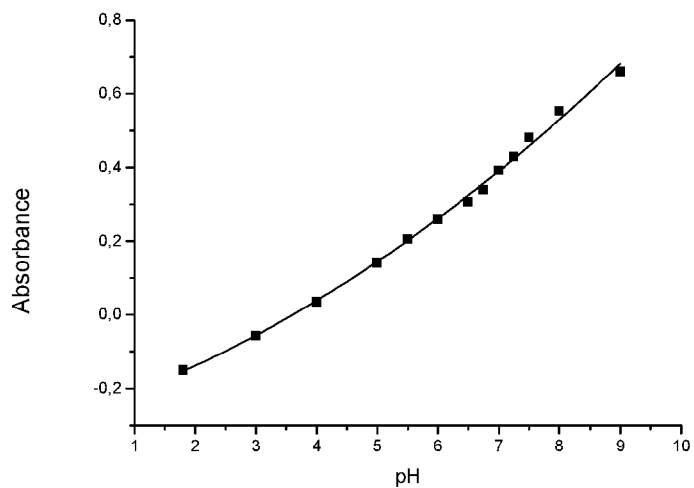
| pH | ΔAbs. |
|---|---|
| 1,8 | -0,1497 |
| 3 | -0,05682 |
| 4 | 0,03473 |
| 5 | 0,1414 |
| 5,5 | 0,2061 |
| 6 | 0,2601 |
| 6,5 | 0,3068 |
| 6,75 | 0,3404 |
| 7 | 0,3932 |
| 7,25 | 0,4314 |
| 7,5 | 0,4812 |
| 8 | 0,5535 |
| 9 | 0,6609 |
| y = a + b*x + c*x*x | |
|---|---|
| a | -0,2699 |
| b | 0,0541 |
| c | 0,0057 |
| $R^2$ | 0,99616 |
Figure 2: The ATIR spectra recorded in the visible spectrum (at 430 nm) of the sensor layer made from polyurethane by the physical stabilization of the PI-2 indicator in sol-gel, and the calibration curve edited therefrom

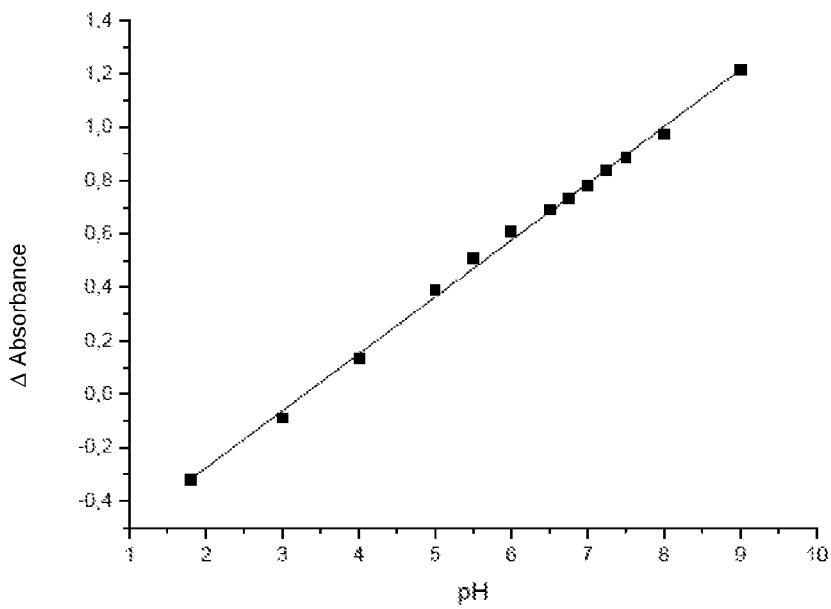
| pH | ΔAbs. |
|---|---|
| 1,8 | -0,32151 |
| 3 | -0,09031 |
| 4 | 0,13287 |
| 5 | 0,38834 |
| 5,5 | 0,50854 |
| 6 | 0,60928 |
| 6,5 | 0,69069 |
| 6,75 | 0,73443 |
| 7 | 0,78069 |
| 7,25 | 0,83814 |
| 7,5 | 0,88768 |
| 8 | 0,97274 |
| 9 | 1,21513 |
| y = a + b*x | |
|---|---|
| a | -0,70184 |
| b | 0,21307 |
| $R^2$ | 0,99744 |
Figure 3: The calibration curve obtained in the visible spectrum (at 408 nm) of the sensor layer made using of the MPI-2 indicator, with ATIR measuring configuration, which provides for a change in the absorbance as result

P-NITROPHENOLE-FORMALDEHYDE POLYCONDENSATE FOR MEASUREMENT, METHOD OF PRODUCTION AND USE

This is the national stage of International Application PCT/HU2015/050009, filed Sep. 29, 2015.

THE FIELD OF THE INVENTION

The invention relates to a wide range optical indicator for measuring pH, the support comprising said indicator, and the sensor comprising said supported indicator.

DESCRIPTION OF THE STATE OF THE ART

It is a characteristic to the optical pH measuring sensors comprising an acid-base indicator, that the measuring range is determined by the dissociation constant (pK) of the indicator. If the measurement is based on the determination of the ratio of the acidic and basic form by the change of the absorption (change of colour) or by the change of fluorescence, and the instrumental analysis thereof, the precise determination of pH is possible around the dissociation constant of the indicator, in the range of pK±1-1.5, that is within pH 2 to 3 units.

A number of acid-base indicators are known from the literature (Niclas Strömberg et al. Analytica Chimica Acta 636 (2009) 89-94, Seungjoon Lee et al. Sensors and Actuators B 128 (2008) 388-398, J. Chance Carter et al. Biosensors and Bioelectronics 21 (2006) 1359-1364, Jesus M. Cones IEEE SENSORS JOURNAL, VOL. 7, NO. 3, MARCH 2007, Mehmet Yildirim et al. J Fluoresc (2012) DOI 10.1007/s10895-011-1034-9, Bastien Schyrr et al. Sensors and Actuators B 194 (2014) 238-248, Yoshiyuki Kowada et al. Journal of Sol-Gel Science and Technology 33, 175-185, 2005). One sort of these compounds is p-nitrophenol, the pK value of which is 7.16 at 22° C. temperature, its transition range is 5.6 to 7.6, where its colour changes from colourless to yellow.

U.S. Pat. No. 4,500,691 discloses phenol novolac derivatives comprising amino groups, for the preparation of which a condensed polymer of nitro phenol with formaldehyde can be used as starting material [see: the compound of Formula (V), wherein $R^1$ stands for a nitro group in p-position, and $R^2$ and $R^3$ stand for hydrogen; from column 1, line 40 until column 2 line 40].

US 2004/0241331 A1 discloses silane-modified phenolic resins, wherein the phenolic skeleton may carry a number of substituents. The scope of disclosed substituents, however, does not include the nitro group. The silane-modified phenolic resins may be applied as additives of vulcanizable rubber compositions.

Optical sensors comprising certain indicator compounds are disclosed for measuring of pH e.g. in U.S. Pat. No. 5,039,492, US 2006/0121623 A1 and WO 2009/118271 A1.

A drawback of the known pH measuring optical indicators is that their measuring range is very narrow, and in general extends to 2, in the most favorable case 3 pH units.

The technical solutions directed to the widening of the measuring range of the pH determination in optical manner have became known in the last 20 years (WO 1993007483 A1).

A fluorescence pH measuring method is known, which gives satisfactory result in a wider pH range than those mentioned above (Chem. Commun., 2014, 50, p. 4711-47139). In another case the hydrogen ions to be determined influence the fluorescence intensity of the indicator molecule according to the so called photon induced electron transfer (PET) (Sensors and Actuators B: Chemical, Volume 114, Issue 1, p. 308-315) mechanism.

Some publications achieve the pH determination in a wider range by using of a combination of indicators with different dissociation constant in the appropriate proportions (Sensors and Actuators B: Chemical, Volume 129, Issue 1, p. 94-98, US20090084175, U.S. Pat. No. 7,432,109 B2).

Therefore, there has been a need for the elaboration of a new solution, which makes it possible to determine the pH in optical way in a range wider than 3 pH units. The discoveries below serve as solution for the above problem:

a) The inventors have elaborated a novel solution for measuring pH in optical way in a range wider than 3 pH units. The substantial point of the solution is that a polymer-like (PI) novel material has been generated by the chemical assembly of the same, pH sensitive, small indicator molecules. In the novel PI molecule the pK values of the individual pH sensitive groups are shifted as compared to the starting material, which makes the pH determination possible in a wide range (pH=1.8 to 10). The solution includes the method for the preparation of the novel PI molecule.

b) In order to form the sensor, the PI molecules need to be stabilized on the surface of a support, or in a layer. The solution includes the method for the elaboration of the suitable chemical stabilization, during which the pH sensitive features of the PI material do not substantially change.

c) Furthermore, the solution includes a sol-gel layer with such a composition, to which the PI indicator may be covalently bonded, in such a manner that it ensures that the stabilized PI molecule be capable of measuring pH in a wide range on one hand, on the other hand, the sensor layer be capable of being applied to the surface of a support with an arbitrary geometry (e.g. planar, optical strand, capillary).

BRIEF DESCRIPTION OF THE INVENTION

Based on the above, the subject matter of the invention is specified as follows:

1. An optical indicator for use for measuring pH, wherein the optical sensor comprises a support, and one or more p-nitrophenyl/formaldehyde condensed polymer according to Formula (I) in the state of being stabilized to said support

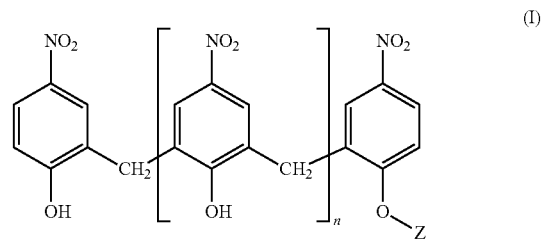

(I)

wherein n has a value of 1 to 20, and Z stands for H or a binding group.

2. The optical indicator according to Point 1, for use for measuring pH in the range of 1.8 to 10.

3. The optical indicator according to Point 1 or 2, wherein the p-nitrophenyl/formaldehyde condensed polymer according to Formula (I) is stabilized to the support by a physical bond.

4. The optical indicator according to Point 1 or 2, wherein the p-nitrophenyl/formaldehyde condensed polymer according to Formula (I) is stabilized to the support by a chemical bond.

5. The optical indicator according to Point 4, wherein in Formula (I) Z stands for a group according to the Formula $L_1'$-R-$L_2$, wherein $L_1'$ stands for a) 2-hydroxyethane 1,2-diyl group

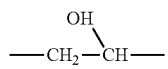

b) 6-hydroxy-phenyl-1,3-diyl group

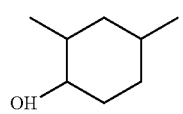

c) thiocarbonylamino group

d) carbonylamino group

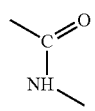

e) carbonyl group

R stands for a direct bond or C1-C20 saturated, unsaturated or aromatic, straight or branched or cyclic, bifunctional hydrocarbon group, $L_2$ stands for a) alkoxy-silanyl group

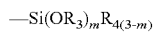

wherein m has a value of 1 to 3, $R_3$ stands for hydrogen or a C1-C6 alkyl group, $R_4$ stands for C1-C20 saturated, unsaturated or aromatic, straight or branched or cyclic, monofunctional hydrocarbon group or a perfluorinated or aminated derivative thereof, b) isothiocyanato group

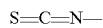

c) isocyanato group

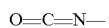

d) acid halogenide group

wherein X stands for halogene atom e) ester group

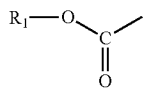

wherein $R_1$ stands for C1-C6 alkyl group f) carboxyl group

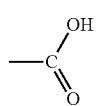

g) mercapto group

6. The optical indicator according to Points 1 to 5, wherein the support is a silica nanopearl, the diameter of which is 0.01 to 2 μm.

7. The p-nitro-phenyl/formaldehyde condensed polymer according to Formula (I)

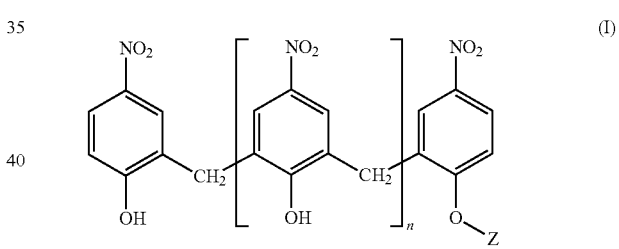

wherein n has the value of 1 to 20, and Z stands for H or a binding group, for use for measuring pH.

8. The polymer according to Point 7, wherein in Formula (I) Z stands for a binding group according to the Formula $L_1'$-R-$L_2$, wherein $L_1'$ stands for a) 2-hydroxyethane 1,2-diyl group

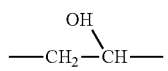

b) 6-hydroxy-phenyl-1,3-diyl group

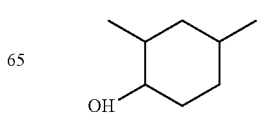

c) thiocarbonylamino group

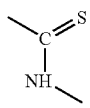

d) carbonylamino group

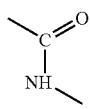

e) carbonyl group

R stands for a direct bond or C1-C20 saturated, unsaturated or aromatic, straight or branched or cyclic, bifunctional hydrocarbon group,
$L_2$ stands for
a) alkoxy-silanyl-group

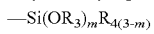

wherein m has a value of 1 to 3, $R_3$ stands for hydrogen or C1-C6 alkyl group, $R_4$ stands for C1-C20 saturated, unsaturated or aromatic, straight or branched or cyclic, monofunctional hydrocarbon group or a perfluorinated or aminated derivative thereof,
b) isothiocyanato group

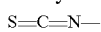

c) isocyanato group

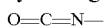

d) acid halogenide group

wherein X stands for a halogene atom
e) ester group

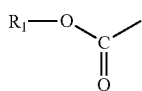

wherein $R_1$ stands for C1-C6 alkyl group
f) carboxyl group

g) mercapto group

9. A functionalized derivative according to Formula (II)

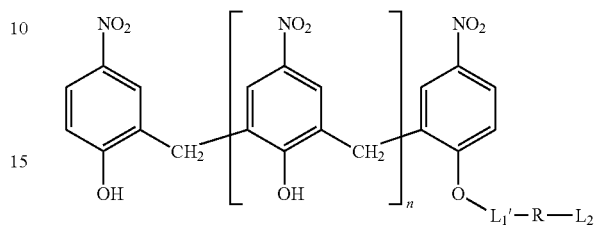

wherein n has a value of 1 to 20,
$L_1'$ stands for
a) 2-hydroxyethane 1,2-diyl group

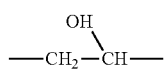

b) 6-hydroxy-phenyl-1,3-diyl group

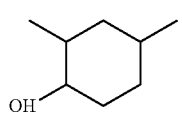

c) thiocarbonylamino group

d) carbonylamino group

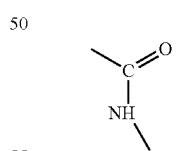

e) carbonyl group

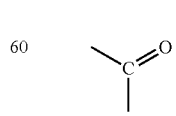

R stands for a direct bond or C1-C20 saturated, unsaturated or aromatic, straight or branched or cyclic, bifunctional hydrocarbon group, $L_2$ stands for
a) alkoxy-silanyl group

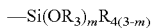

wherein m has a value of 1 to 3, $R_3$ stands for hydrogen or C1-C6 alkyl group, $R_4$ stands for C1-C20 saturated, unsaturated or aromatic, straight or branched or cyclic, monofunctional hydrocarbon group or a perfluorinated or aminated derivative thereof, b) isothiocyanato group

c) isocyanato group

d) acid halogenide group

wherein X stands for halogene atom e) ester group

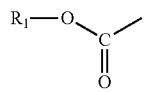

wherein $R_1$ stands for C1-C6 alkyl group f) carboxyl group

g) mercapto group

10. The functionalized derivative according to Formula (II) according to Point 9, wherein L1 is other than 1,2-epoxy group, 3,4-epoxycyclohexyl group or isocyanato group, if R stands for C1-C18 saturated, unsaturated, straight or branched hydrocarbon group, and L2 stands for a —Si(OR$_3$)$_m$R$_{4(3-m)}$ alkoxy-silanyl group, wherein R3 stands for C1-C4 alkyl group, and R4 stands for C1-C4 alkyl group, phenyl group or cyclohexyl group.

11. A process for the preparation of the functionalized derivative according to Formula (II) according to Point 9, which comprises the step of reacting of the p-nitrophenyl/formaldehyde condensed polymer according to Formula (I), wherein Z stands for H, with a reagent according to the Formula $L_1$-R-$L_2$,
wherein $L_1$ stands for
a) 1,2-epoxy group

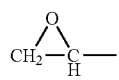

b) 3,4-epoxycyclohexyl group

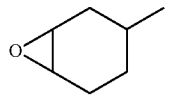

c) isothiocyanate group

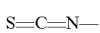

d) isocyanato group

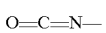

e) acid halogenide group

wherein X stands for halogene atom
f) ester group

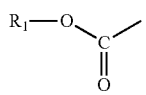

wherein $R_1$ stands for C1-C6 alkyl group
g) carboxyl group

R and $L_2$ have the meanings as specified in Point 9.

12. Supported polymer, which comprises a support and one or more p-nitrophenyl/formaldehyde condensed polymer according to Formula (I) in the state of being stabilized to said support

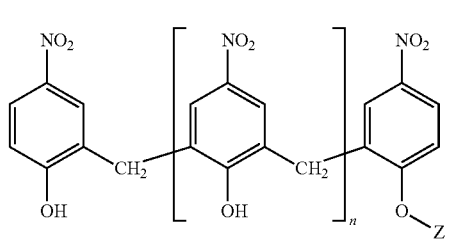

wherein n has a value of 1 to 20, and Z stands for H or a binding group.

13 The supported polymer according to Point 12, wherein the p-nitrophenyl/formaldehyde condensed polymer according to Formula (I) is stabilized to the support by a physical bond.

14. The supported polymer according to Point 12, wherein the p-nitrophenyl/formaldehyde condensed polymer according to Formula (I) is stabilized to the support by a chemical bond.

15. The supported polymer according to Point 14, wherein the p-nitrophenyl/formaldehyde condensed polymer according to Formula (I) is stabilized to the support in the form of one or more functionalized derivative according to Formula (II) by a covalent bond.
16. The supported polymer according to any of Points 12 to 15, wherein the support is a silicon nanopearl, having a diameter of 0.01 to 2 μm.
17. The supported polymer according to any of Points 12 to 16 for use as a part of an optical sensor useful for measuring pH.
18. An optical sensor useful for measuring pH, which comprises the supported polymer according to any of Points 12 to 17.
19. Use of the supported polymer according to any of Points 12 to 17 for the preparation of an optical sensor useful for measuring pH.

BRIEF DESCRIPTION OF THE DRAWINGS

FIG. 1 shows the normalized calibration curves of p-nitrophenol (a), the PI-1 indicator (b) and the PI2 indicator (c) in a water-tetrahydrofurane mixture.

FIG. 2 shows the ATIR spectra recorded in the visible spectrum (at 430 nm) of the sensor layer made from polyurethane by the physical stabilization of the PI-2 indicator in sol-gel, and the calibration curve edited therefrom.

FIG. 3 shows the calibration curve obtained in the visible spectrum (at 408 nm) of the sensor layer made using of the MPI-2 indicator, with ATIR measuring configuration, which provides for a change in the absorbance as result.

DETAILED DESCRIPTION OF THE INVENTION

Accordingly, the subject matter of the invention is an optical indicator for use for measuring pH, wherein the optical indicator comprises a support, and one or more p-nitrophenyl/formaldehyde condensed polymer according to Formula (I) in a state bound to said support

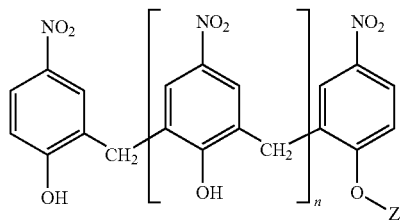
(I)

wherein n has a value of 1 to 20, and Z stands for H or a binding group.

In one embodiment of the invention the p-nitro-phenyl/formaldehyde condensed polymer according to Formula (I) is the polymer according to Formula (I')

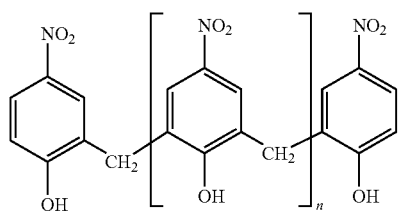
(I')

wherein n has a value 1 to 20.

In another embodiment of the invention in the p-nitrophenyl/formaldehyde condensed polymer according to Formula (I) Z stands for a binding group.

As used in the present description, the term "binding group" shall mean an arbitrary binding group, which is suitable for forming of a covalent bond, between the polymer according to the Formula (I') and the support. As an example for the binding group, the group according to the formula $L_1'$-R-$L_2$ may be mentioned.

According to a further embodiment of the present invention the p-nitrophenyl/formaldehyde condensed polymer according to Formula (I) is the functionalized derivative thereof according to Formula (II)

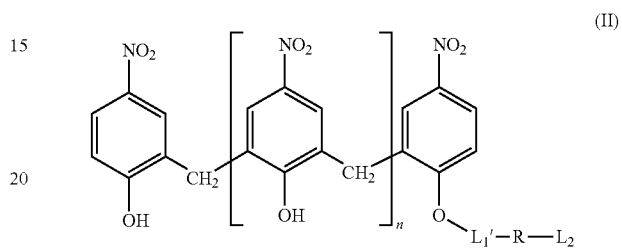
(II)

wherein n has a value of 1 to 20, $L_1'$ stands for a) 2-hydroxyethane 1,2-diyl group

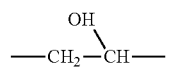

b) 6-hydroxy-phenyl-1,3-diyl group

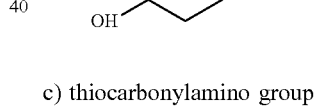

c) thiocarbonylamino group

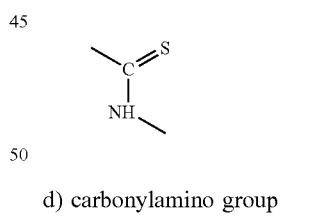

d) carbonylamino group

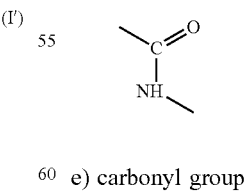

e) carbonyl group

R stands for a direct bond or a C1-C20 saturated, unsaturated or aromatic, straight or branched or cyclic, bifunctional hydrocarbon group,
$L_2$ stands for
a) alkoxy-silanyl group

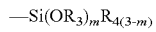

wherein m has a value of 1 to 3, $R_3$ stands for hydrogen or C1-C6 alkyl group, $R_4$ stands for C1-C20 saturated, unsaturated or aromatic, straight or branched or cyclic, monofunctional hydrocarbon group or a perfluorinated or aminated derivative thereof,
b) isothiocyanato group

c) isocyanato group

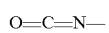

d) acid halogenide group

wherein X stands for halogene atom
e) ester group

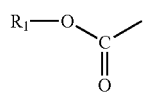

wherein $R_1$ stands for C1-C6 alkyl group
f) carboxyl group

g) mercapto group

The functionalized derivatives according to Formula (II) are novel compounds, therefore they are subject matter of the present invention.

Furthermore, the present invention relates to a process for the preparation of the functionalized derivatives according to Formula (II), wherein the p-nitro-phenyl/formaldehyde condensed polymer according to Formula (I) wherein Z stands for H, is reacted with the reagent according to the Formula $L_1$-R-$L_2$,
wherein $L_1$ stands for
a) 1,2-epoxy group

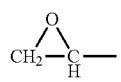

b) 3,4-epoxycyclohexyl group

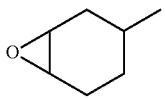

c) isothiocyanate group

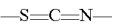

d) isocyanato group

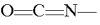

e) acid halogenide group

wherein X stands for halogene atom
f) ester group

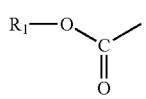

wherein $R_1$ stands for C1-C6 alkyl group
g) carboxyl group

R and $L_2$ have the meaning defined above.

Furthermore, the present invention relates to a supported polymer, which comprises a support and a p-nitro-phenyl/formaldehyde condensed polymer according to Formula (I) in a state bound to said support.

In the supported polymer according to the invention the p-nitro-phenyl/formaldehyde condensed polymer according to Formula (I) is bound either by a physical bond or a chemical bond.

In the supported polymer according to the invention the p-nitro-phenyl/formaldehyde condensed polymer according to Formula (I), especially in the form of the functionalized derivative according to Formula (II), is bound by a covalent bond.

Furthermore, the invention relates to an optical sensor comprising the supported polymer according to the invention for measuring pH.

In the context of the above formulae the term "alkyl group" means a monofunctional hydrocarbon group with the specified number of carbon atoms, which may be linear or branched.

The term "alkanediyl group" means a saturated bifunctional hydrocarbon group, with the given number of carbon atoms, said group being either of straight or branched chain.

The term "alkenediyl group" means an unsaturated bifunctional hydrocarbon group, with the given number of carbon atoms, containing one or more double bonds, said group being either of straight or branched chain.

The term "saturated, unsaturated or aromatic, straight or branched or cyclic bifunctional hydrocarbon group" means a saturated, unsaturated or aromatic, straight or branched or cyclic bifunctional hydrocarbon group, which is linked to the $L_1$ and $L_2$ groups via carbon atoms in α-ω positions.

The term "saturated, unsaturated or aromatic, straight or branched or cyclic monofunctional hydrocarbon group" means a saturated, unsaturated or aromatic, straight or branched or cyclic bifunctional hydrocarbon group, which is linked by one of the terminal carbon atoms.

The term "perfluorinated derivative" means a hydrocarbon group, in which each hydrogen is replaced by a flourine atom.

In the above formulae in general n has the value of 1 to 20, especially 2 to 15, preferably 3 to 10.

In the above formulae R stands for a direct bond or a C1-C20 saturated, unsaturated or aromatic, straight or branched or cyclic bifunctional hydrocarbon group. As examples the following may be mentioned:

a) alkanediyl group

wherein k has the value of 0 to 20, b) phenylene group

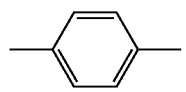

c) methylene-diphenyl group

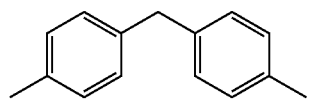

In the above formulae X stands for halogene atom, such as fluorine, chlorine, bromine or iodine atom, especially fluorine or chlorine atom.

In the above formulae, in general $R_1$ stands for C1-C6 alkyl group, especially C1-C4 alkyl group. As examples the methyl, ethyl, n- or isopropyl or n-, iso- sec- or tert-butyl group may be mentioned.

In the above formulae, in general $R_2$ stands for C1-C6 alkanediyl vagy alkenediyl group, especially C1-C4 alkanediyl- or alkenediyl group. As examples the methylene, ethylene, propylene or ethenediyl group may be mentioned.

In the above formulae, in general $R_3$ stands for hydrogen or C1-C6 alkyl group, especially hydrogen or C1-C4 alkyl group. As example for the alkyl group the methyl, ethyl, n- or isopropyl or n-, iso-, sec- or tert-butyl group may be mentioned.

In the above formulae, in general $R_4$ stands for C1-C20 saturated, unsaturated or aromatic, straight or branched or cyclic, monofunctional hydrocarbon group or a perfluorinated or aminated derivative thereof. As example the methyl group, ethyl group, phenyl group, pentafluorophenyl group and 3-aminopropyl group may be mentioned.

The p-nitro-phenyl/formaldehyde condensed polymer according to Formula (I), wherein Z stands for H [compound according to Formula (I')], can be prepared by known reactions. Said reactions are proceeded by either condensing phenol with formaldehyde, and nitrating the obtained condensed polymer [process (a)], or by condensing p-nitrophenol with formaldehyde [process (b)].

The starting materials used in the course of the process are commercially available, for example from Sigma-Aldrich, Alfa Aesar, VWR International.

The process (a) suitable for the preparation of p-nitrophenyl/formaldehyde condensed polymer according to Formula (I') is performed in two steps. One of the embodiments of the process is illustrated by Scheme 1:

Scheme 1

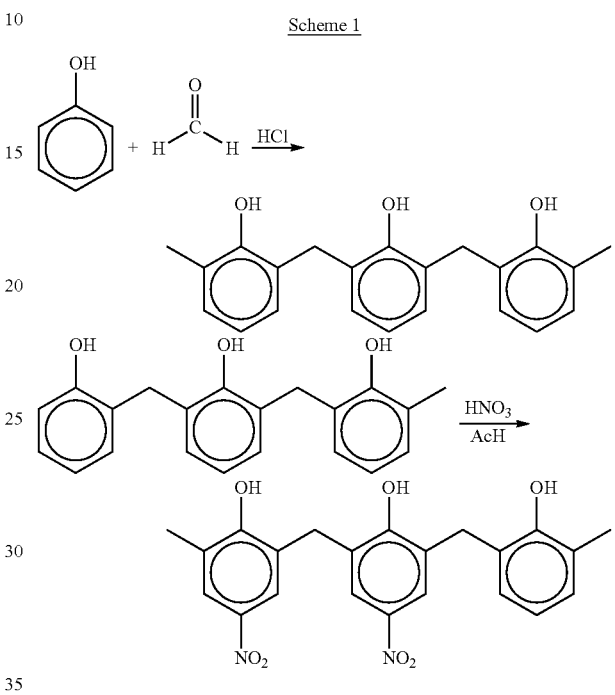

In the first step phenol is condensed with formaldehyde, as a result of which phenol/formaldehyde condensed polymer is obtained. The obtained resin is equivalent with novolac in terms of their chemical composition, however, it is of smaller molecular weight.

The process is usually performed at room temperature, especially at 20-25° C., and at atmospheric pressure. However, the process can also be made at a lower temperature and pressure. The process is optionally made in the presence of a catalyst. As catalyst sulphuric acid, hydrochloric acid, oxalic acid may be used. The obtained resin is conventionally separated, e.g. is washed with distilled water, then is dissolved in ethanol and added dropwise into water.

In the second step of process (a) the phenol/formaldehyde condensed polymer is nitrated. The nitration is performed in a manner known for the skilled person. During said operation a nitrating mixture (an aqueous mixture of concentrated $H_2SO_4/HNO_3$) is especially used in the presence of a suitable solvent. As solvent e.g. formic acid, butiric acid, especially propionic acid and acetic acid can be used.

In general the nitration of the phenol/formaldehyde condensed polymer in not complete. The rate of nitration is in general 27-36%, especially 47-53%. The rate of nitration is monitored by elementary analysis. The process is especially performed at 4-5° C. temperature and atmospheric pressure. However, the process can also be made at a lower or higher temperature and pressure. The nitration is in general performed in the presence of the atmosphere of an inert gas, in particular in argon or nitrogen atmosphere. The final product is conventionally purified, e.g. is diluted with water, then is filtered through a filter paper, and is washed until the pH of the filtrate becomes mostly neutral. Then the product is dried at room temperature.

The preparation of p-nitro-phenyl/formaldehyde condensed polymer according to Formula (I) can also be accomplished in one step according to process (b). In said process p-nitro-phenol is condensed with formaldehyde. The condensation according to process (b) is performed according to the method as described in the first step of process (a).

One embodiment of the process is illustrated by Scheme 2:

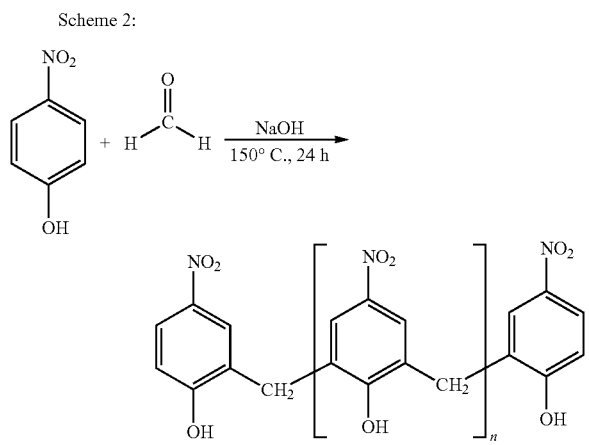

The p-nitro-phenol used as starting material may be prepared by a known method or can be commercially obtained.

The process is usually performed at a temperature above 100° C., especially 150-160° C. temperature, and at atmospheric pressure. However, the process can also be made at a lower or higher temperature and pressure. In general, the process is performed for 24 hours with formaldehyde, in the presence of NaOH. The produced polymer is purified by conventional methods, e.g. it is washed with acetic acid and ethanol, is centrifuged after washing, then is dried at 60-70° C.

The p-nitro-phenyl/formaldehyde condensed polymer according to Formula (I') can be used as indicator at measuring pH.

To achieve this, according to one of the embodiments of the present invention a process is performed, wherein the p-nitro-phenyl/formaldehyde condensed polymer according to Formula (I') is stabilized to a support. The linkage can be achieved by a physical bond or a chemical bond.

The material of the support can be solid or can be in sol or gel state, its surface can be smooth or porous. As examples glass, quartz, amorphous silicon dioxide, polycarbonate, polyester, poly-methyl-methacrylate or other optically translucent polymer may be mentioned. The support may be of plain or curved surface, in particular of spherical surface. According to one of the embodiments of the present invention the support is a nanopearl, which has a diameter of 0.001 to 10 μm, in particular 0.01 to 5 μm. According to another embodiment of the present invention the support is a silica nanopearl, which has a diameter of 0.01 to 2 μm.

In case of a physical type of bondage (chemical bondage is not generated between the indicator and the support) the indicator in the form of p-nitro-phenyl/formaldehyde condensed polymer according to Formula (I') is taken up in a suitable solvent, or is mixed in a sol-gel mixture. Then the obtained mixture is contacted with the support. In particular, a process is performed, wherein the dissolved form of the indicator, or the reagents necessary for the formation of sol-gel, said reagent can be e.g. water, hydrochloric acid, or a solution of ammonia, is added to the mixture of the applied tetraalkoxy-silanes, such as, e.g. to the mixture of TEOS, MTES, APTES, PhTES, DiME-DiMOS, then the mixture is allowed to be gelled. After gelling the mixture is dried, and if desired, pulverized. Then it is added to the support by conventional manner. This can be e.g. pouring up, spin-coating, knife-coating.

For dissolving the indicator as solvent ethanol, aceton, THF, DMF, in particular ethyl acetate may be used. The stabilization to the support may be facilitated by the activation of the support, said activation may be done chemically e.g. by nitric acid, Caro-acid (the mixture of hydrogen-peroxide and sulphuric acid), or physically, e.g. by ionizing radiation, plasma or ultrasonic activation.

According to one of the embodiments of the present invention in order to form the chemical bond the p-nitro-phenyl/formaldehyde condensed polymer according to Formula (I') is converted to the functional derivative according to Formula (II). To achieve this, the p-nitro-phenyl/formaldehyde condensed polymer according to Formula (I') is reacted with a compound according to Formula $L_1$-R-$L_2$. One embodiment of the process is illustrated by Scheme 3:

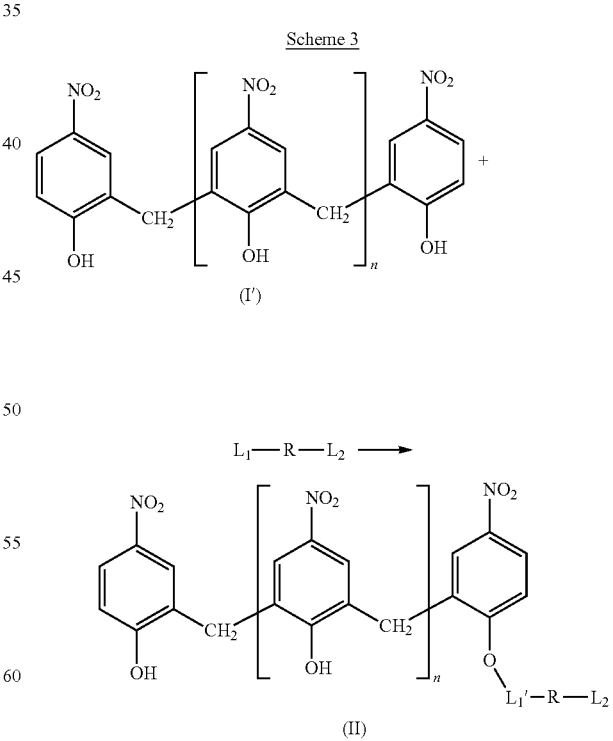

The compound according to formula $L_1$-R-$L_2$ used as reagent can be prepared by known processes or is commercially available (Sigma Aldrich, Alfa Aesar).

The compound according to formula $L_1$-R-$L_2$ that may preferably used can be exemplified by the following:

1.1. [3-(2,3-epoxypropoxy)propyl]triethoxysilane

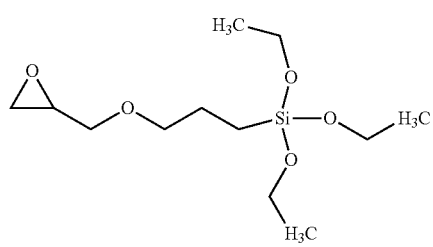 [SMILES: CCO[Si](CCCOCC1CO1)(OCC)OCC]

1.2. [2-(3,4-epoxycyclohexyl)ethyl]trimethoxysilane

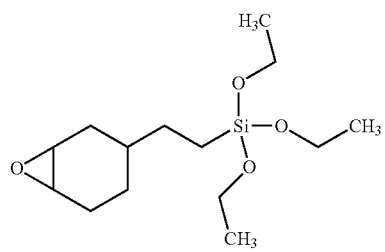 [SMILES: CCO[Si](CCC1CCC2OC2C1)(OCC)OCC]

1.3. 1-isothiocyanato-4-[(4-isothiocyanatophenyl)methyl]benzene

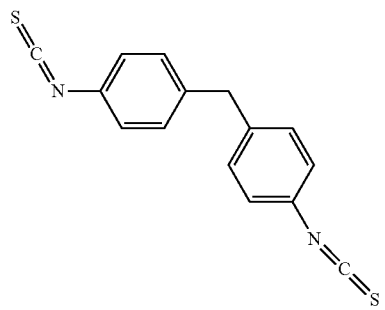 [SMILES: S=C=Nc1ccc(Cc2ccc(N=C=S)cc2)cc1]

1.4. 5-[(3,5-diethyl-4-isocyanatophenyl)methyl]-1,3-diethyl-2-isocyanatobenzene

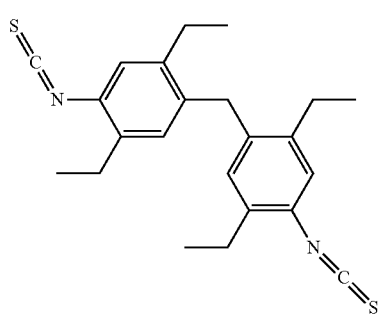 [SMILES: CCc1cc(N=C=S)c(CC)cc1Cc1cc(CC)c(N=C=S)cc1CC]

1.5. fumaryl-chloride

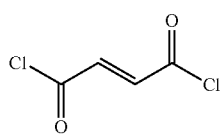

1.6. maleic acid anhydride

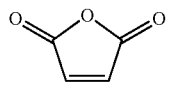

1.7. adipic acid anhydride

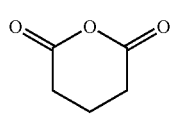

1.8. dimethyl-terephthalate

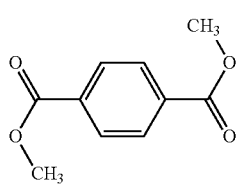

1.9. ethyl-fumaryl-chloride
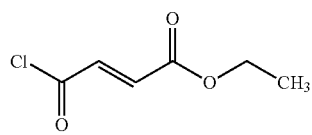
1.10. adipic acid-monoethylester
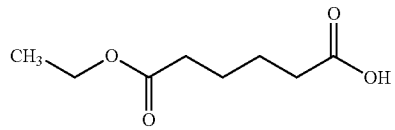
The preparation of certain functional derivatives according to Formula (II) with different compounds according to Formula $L_1$-R-$L_2$ is illustrated by Schemes 3.1. to 3.8:
Scheme 3.1.
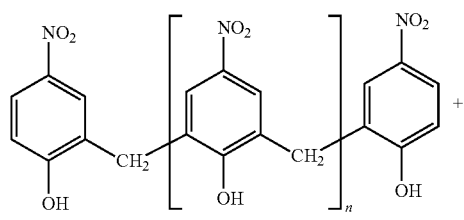
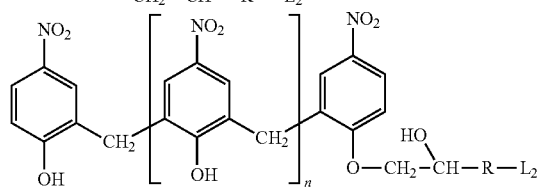
Scheme 3.2.
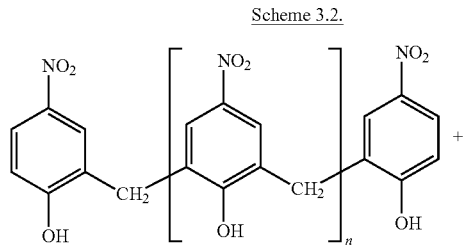
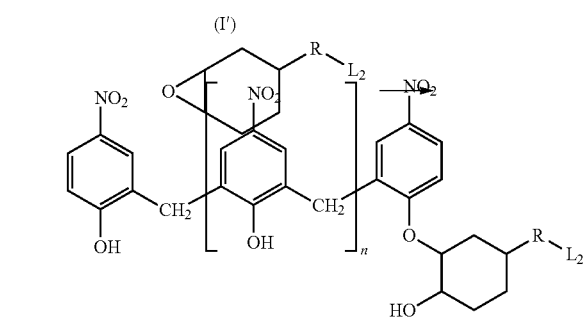
Scheme 3.3.
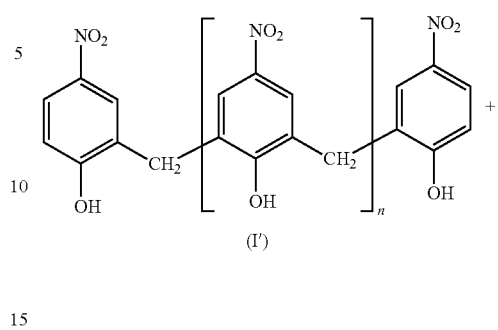
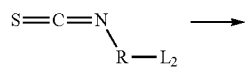
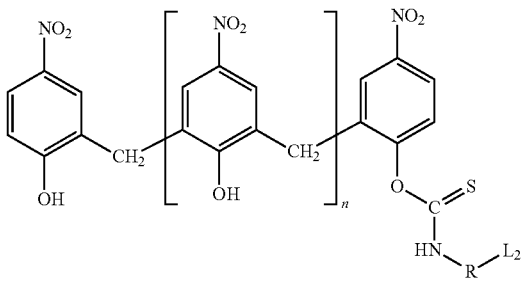
Scheme 3.4.
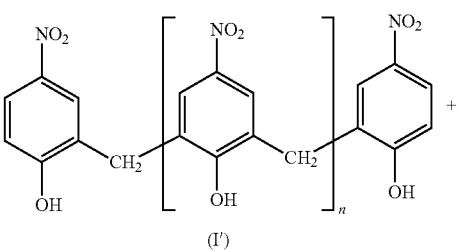
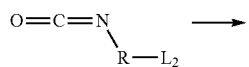
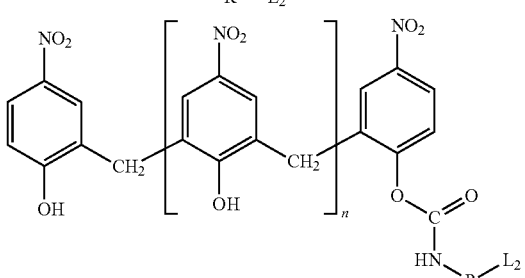

Scheme 3.5.
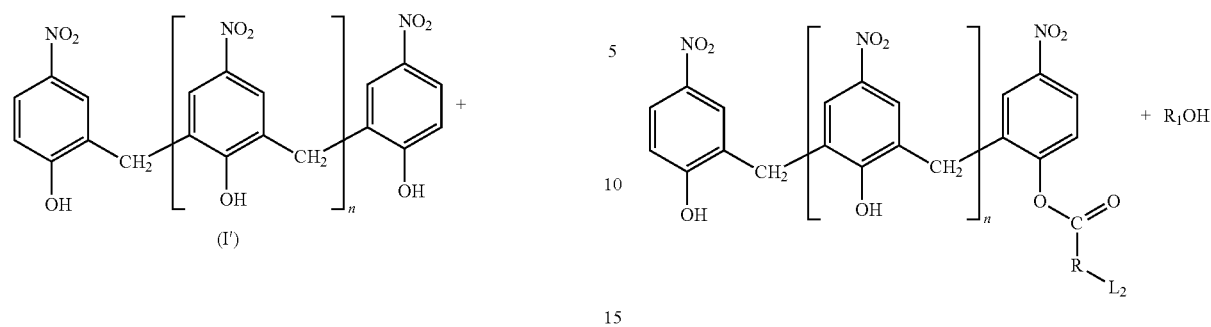
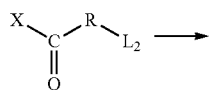
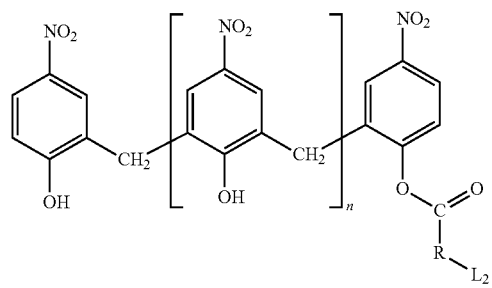
+ HX
Scheme 3.6.
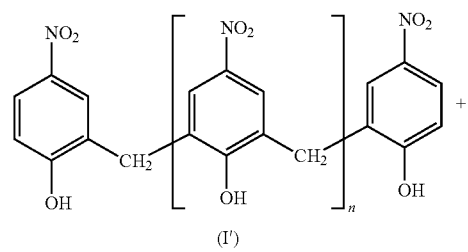
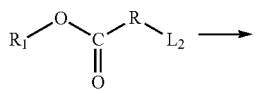
Scheme 3.7.
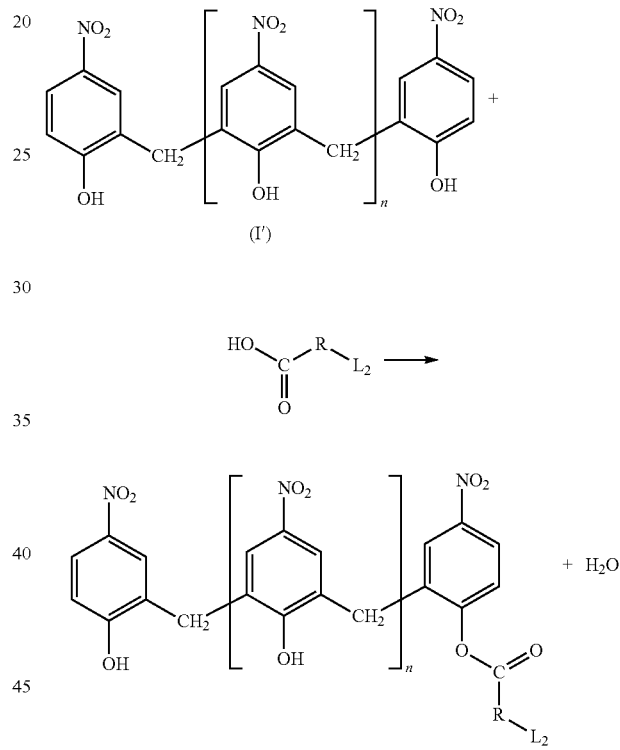
One embodiment of the process is shown by Scheme 3.8:
Scheme 3.8.
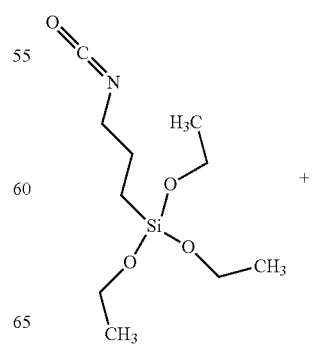

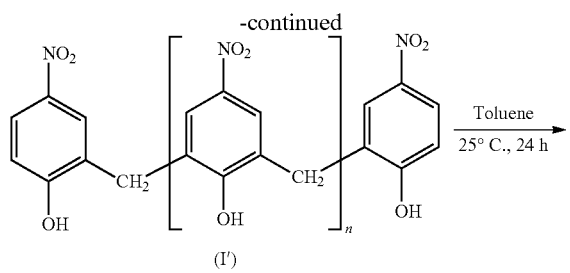

(I')

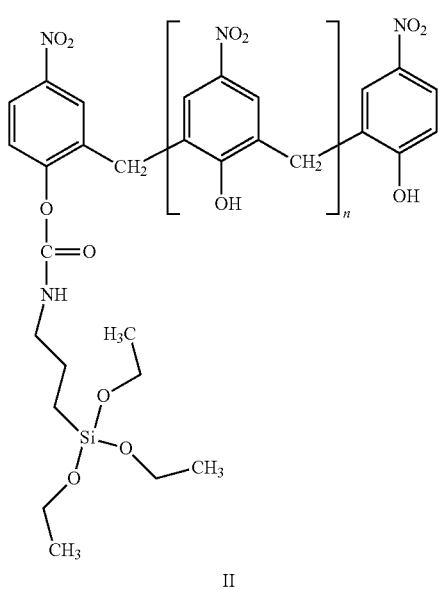

II

The process in general is performed at room temperature, in particular at 20-25° C. temperature, and atmospheric pressure. However, the process can also be made at a lower or higher temperature and pressure.

In case of chemical bondage, the indicator is stabilized on the surface of the support in the form of the functionalized derivative according to Formula (II) with a covalent bond.

According to one embodiment of the chemical bondage, the functionalized derivative according to Formula (II) is taken up in a suitable solvent, and is contacted with the surface of a solid support, e.g. silica nanopearl.

According to another embodiment of the chemical bondage, a process is performed, wherein the functionalized derivative according to Formula (II) is taken up in a suitable solvent, and is mixed into the sol-gel mixture.

As solvent for dissolving of the indicator ethanol, acetone, especially tetrahydrofurane, ethyl-acetate can be used. As reagent for the preparation of sol-gel APTES, PhTES, DiME-DiMOS, especially TEOS, MTES can be used.

According to a further embodiment of the chemical bondage, a process is performed, wherein the support is first treated with excess diisocyanate derivative, then it is immersed into a solution of the polymer according to Formula (I') made with an anhydrous solvent without separation, or said solution is spread on the surface of the support.

The indicator applied to the support can be built into an optical sensor applicable for measuring pH. In this process, in general a conventional process is performed, as it is exemplified by pouring up, spin-coating, knife-coating, dip-coating, and the like.

The optical sensor can be any kind of optical sensor or device, which detects the quantity or quality of chemical components in gas or liquid phase, and it is converted to an electric signal, which is useful for analytical purposes (Pure&App. Chem., Vol. 63, No. 9, pp. 1247-1250, 1991).

The optical indicator according to the present invention and the sensor device including said optical sensor can be used for measuring pH.

In this process the indicator built in the optical sensor dissociates to $H^+$ ion and anion, the rate of said dissociation being determined by the pH of the sample. The colour of the acidic and basic form is different from each other, which can be detected spectrofotometrically. The calibration takes place with buffers with various pH values. Measuring pH and the calibration are published in detail by Sensors and Actuators B 128 (2008) 388-398, Sensors and Actuators B 194 (2014) 238-248.

Without wishing to be bound to one given theory, it is believed that the phenolic OH groups of the p-nitro-phenyl/formaldehyde condensed polymer according to Formula (I) dissociate gradually as a function of the pH value. Accordingly, the large number of the phenolic OH groups makes it possible to determine the pH in a wide range, such as in 1.8 to 10 pH range, preferable in 2 to 10 range.

As for the theory of the measuring, it can be the determination of the change in absorbance, transmission, reflection, attenuation of total reflection (ATIR) and refractive index. According to one embodiment of the present invention the determination of the pH is performed using the theory of absorbance. In said process light beam is directed to a layer of the p-nitro-phenyl/formaldehyde condensed polymer according to Formula (I), and the change in the transmission through the layer is determined. The amount of the change is in linear proportion of the colour of the polymer layer, thus detecting of the change makes it possible to follow the pH value. The change of the absorbance is compared to a sample with known pH value as zero value, wherein the change obtained in the sample to be measured can be positive or negative as compared to the zero value. On the basis of the change obtained the pH value of the sample to be measured can be read from the calibration curve.

The optical sensor device according to the invention can be applied for measuring pH in all conventional media. As examples, air, natural and artificial waters, drinking water, biological media (e.g. blood, body fluids, and the like) can be mentioned.

The invention is now described with the following examples, without the intention to restrict the scope as claimed to the examples.

Example 1: The Preparation of the Phenol/Formaldehyde Condensed Polymer (G-1)

10 g phenol is measured into a metal container, then is put into water bath together with a magnetic stirrer. 7 ml of 38% formaldehyde and 4 ml of 20% hydrochloric acid is added thereto, then the water bath is set to 40° C. The temperature is kept between 30 to 40° C. for 60 minutes by adding ice to the water bath as needed, then the temperature is elevated to 60° C., and the mixture is maintained at this temperature for 25 minutes. During this period of time 2 phases separate. The aqueous phase is discarded and the resin (G-1) is washed several times with distilled water. The resin is purified by a suitable method (e.g. dialysis), and dried at room temperature.

Example 2: The Preparation of
p-Nitro-Phenyl/Formaldehyde Condensed Polymer
(PI-1) from G-1

For the preparation of the PI-1 indicator to the mixture of 6 ml water and 6 ml concentrated nitric acid 2 ml (0.30342 g/10 ml) G-1 resin dissolved in acetic acid is added dropwise in argon atmosphere. In the course of nitration the temperature of the mixture is kept below 5° C. The colour of the PI-1 indicator formed during the reaction is dark red, then at room temperature is changes to orange. The PI-1 indicator produced well dissolves in THF and acetone, less easily in ethanol. Its solution is yellow in acidic state, dark yellow, sometimes yellowish brown in basic phase.

Example 3: The Preparation of
p-Nitro-Phenyl/Formaldehyde Condensed Polymer
(PI-2) in One Step 3.5 g 4-nitrophenol is pulverized in achate mortar, then it is put into a 100 ml double neck round bottom flask equipped with magnetic stirrer. Paraffin oil bath is place under the tube, also with magnetic stirrer, and a thermometer calibrated between 100 to 200° C. One neck of the round bottom flask is equipped with a ball cooler, the other neck serves for the entering of the reagents. The 4-nitrophenol is melted at 116° C., then 3 ml of 38% formalyne is added thereto dropwise. After 5 minutes of stirring 750 µl of 0.4 g/ml NaOH is added to the mixture dropwise. The temperature is elevated to between 150 to 160° C., and is maintained there for 24 hours. Once a few hours have passed, thick, fluidic, brown posh is formed in the container. After the reaction has proceeded, the reaction mixture is allowed to cool to room temperature, and acetic acid is added thereto in such an amount that all of the resin is completely dissolved, then the mixture is stirred for further 30 minutes. Then by adding distilled water, the PI-2 indicator is precipitated, and is stirred for 24 hours. The PI-2 indicator is then purified by dialysis. The precipitated material is centrifuged at 5000 rpm for 30 minutes, then is decanted and dried at 60-70° C. in an exsiccator. The obtained PI-2 will be yellow in acidic state and orange in basic state.

The characteristics of the prepared G-1, PI-1 and PI-2 materials: glass transition temperature (Tg), number average molecular weight (Mn) and weight average molecular weight (Mw):

|  | Tg (° C.) | $M_n$ | $M_w$ |
| --- | --- | --- | --- |
| G-1 | 87.6 | 1550 | 2000 |
| PI-1 | 97.2 | 910 | 1300 |
| PI-2 | 134.9 and 110.7 | 770 | 840 |

Data of the IR spectra characteristic to 4-nitrophenol, G-1 resin and PI-2 indicator

|  | aromatic ring vibrations $cm^{-1}$ | vibrations of the aromatic nitro compounds $cm^{-1}$ | vibrations of the polymer chain $cm^{-1}$ | valent vibration of the phenolic OH-group $cm^{-1}$ | vibration signalling the substituting in p-position $cm^{-1}$ |
| --- | --- | --- | --- | --- | --- |
| 4-nitrophenol | 1590 and 1500 | 1518 and 1340 | — | — | 860 |
| G-1 resin | 1610 and 1510 | — | 910 | 1228 | — |
| PI-2 indicator | 1590 and 1500 | 1520 and 1340 | 910 | — | — |

By studying of the pH dependence of the light absorption of the p-nitrophenol starting material, and PI-1 and PI-2 indicators with a spectrophotometer, in a tetrahydrofurane buffer mixture, in dissolved state, it can be stated that the novel indicators change their light absorption in a wider pH range as compared to the starting molecule (FIG. 1). The horizontal axis x of the graph according to FIG. 1 shows the pH value, while its vertical axis y shows the absorbance value. It can be seen that the PI-1 and PI-2 indicators according to the present invention show the change in a lot wider range as compared to the known p-nitro-phenol indicator used as comparative material.

Example 4: The Modification of PI Molecules for
the Stabilization with Covalent Bond 50.00 mg of PI-2 is dissolved in a 2:1 mixture of 5.00 ml THF and toluene. 15.00 µl of (3-isocyanatopropyl)triethoxysilane (3-IPTS) is added thereto, and the solution is stirred for 24 hours. The modified indicator molecules, the MP-2 are used in the same solution, as where the modification had happened. By the modification such a triethoxy silyl group is attached to the indicator molecule, with which the indicator can be attached to e.g. glass or silica surface.

Example 5: The Preparation of Sol-Gel with
Physically Stabilized PI-2 Indicator

To the mixture of 300 µl MTES (methyltriethoxysilane) and 34 µl TEOS (tetraethoxysilane) PI-2 indicator dissolved in 125 µl THF (36.4 mg/1.575 ml), 90 µl ultra pure water, then 30 µl 1 M hydrochloric acid is added, then the mixture is stirred for 2 hours with magnetic stirrer. The thus prepared sol is let in a closed sample container vial at room temperature, until it gels. After the gelation it is poured onto an glass plate, and is allowed to dry at 60° C. for 48 hours. The dried gel is pulverized in an achate mortar.

The preparation of the D1 sensor layer: 50 mg of the sol-gel containing of the pulverized PI-2 indicator is suspended in a 10% ethanolic solution of 450 mg polyurethane hydrogel (e.g. Hydrogel D-4, Tyndall-Plains-Hunter). After homogenization 100 micron thick layer is formed from the mixture on the glass support, then it is allowed to stand for 1 day.

The thus prepared layer is put into a spectrophotometer and is spectrophotometrically studied in ATIR operational mode. FIG. 2 demonstrates the change in the absorbance in the function of the pH as compared to the absorption determined in dry state, wherein the horizontal axis x shows the pH value, while the vertical axis y shows the value of change in the absorance (ΔAbsorbance). It can be stated from FIG. 2 that the sensor layer comprising PI-2 is useful for the determination of the pH in the pH range of pH=2 to 10. As compared with the curves according to FIG. 1, it can also be seen that the stabilization of the indicator molecule in a sol-gel ensures the ability for the determination of the pH in even wider pH range as compared to the dissolved indicator.

Example 6: The Chemical Stabilization of PI-2 on the Surface of Silica Nanopearl To 6.5 ml ethanol 0.5 ml of TEOS is added, then 0.65 ml 25% ammonia solution is added thereto with continuous stirring. After 30 minutes stirring the reaction mixture is placed in an ultrasonic bath for further 30 minutes, and it is further stirred for 23 hours with magnetic stirrer. At the end of the synthesis the container is placed on a heatable magnetic stirrer, and at 80° C. it is heated for 1 hour with continuous stirring. The solution is centrifuged (5000 round/minute, 20 minute), then is decanted. 5.00 ml absolute ethanol is added to the nanopearls, the suspension is sonicated for 30 minutes, and is dried on air. In order to stabilize the indicator, 50.00 mg of PI-2 is dissolved in a 2:1 mixture of 5.00 ml of THF and toluene. 15.00 μl of 3-IPTS is added thereto, and the solution is stirred for 24 hours. A suspension is prepared from the nanopearls by adding 2.00 ml of absolute ethanol. While stirring 2.50 ml of the solution comprising the MPI-2 is added thereto, then the mixture of 2.00 ml of the absolute ethanol and 8.70 μl of 25 m/m % ammonia solution. The solution is stirred for 24 hours, it is purified and dried on air. The average size of the thus prepared nanopearls coated with MPI-2 indicator [Scheme 2 (c)] is determined as 203 nm.

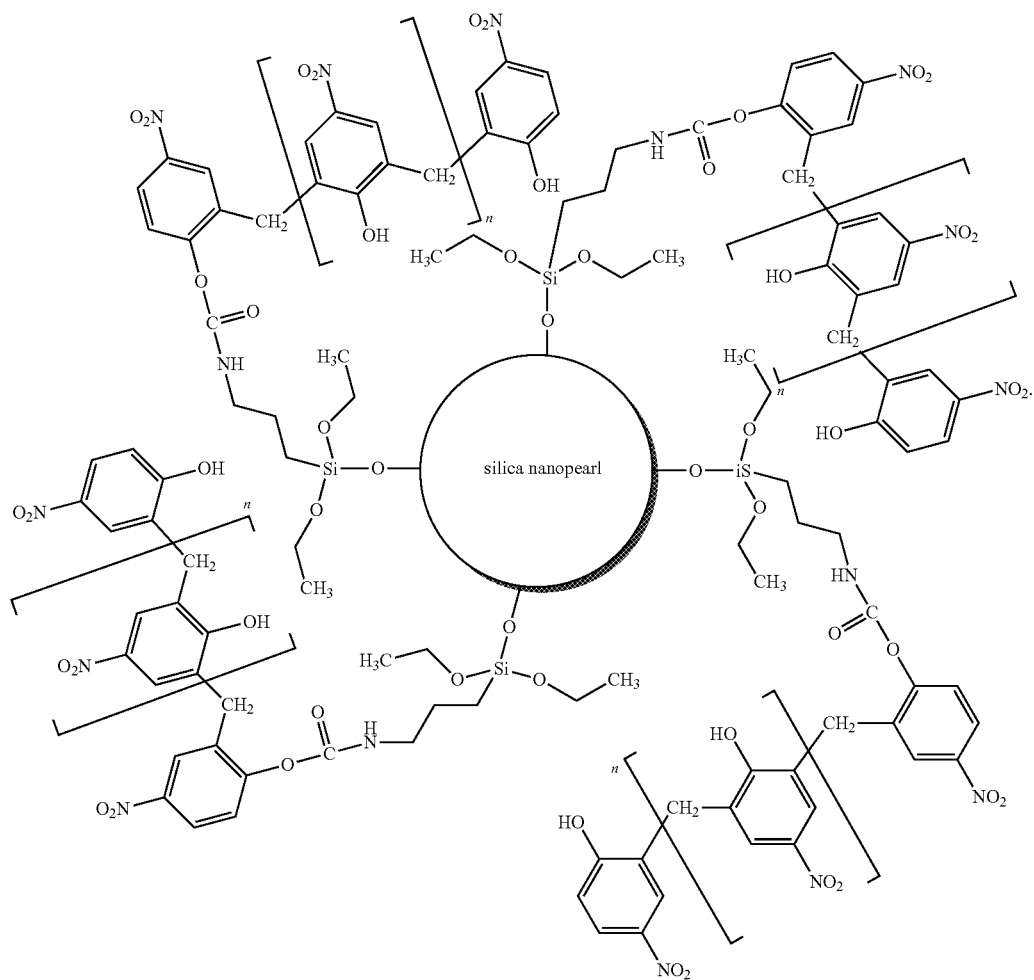

III

Example 7: The Chemical Stabilization of the MPI in Sol-Gel 0.37838 g of PI is dissolved in 2 ml of THF, then 2 ml of THF containing 167.5 ml 3-IPTS is added thereto dropwise with stirring, and it is further stirred for 2 hours (MPI-2 cocktail).

For the sol-gel 6.9 ml of TEOS-t, 1.116 ml ultrapure water and 120.3 µl 37% hydrochloric acid is measured together. To 1.5 ml of this mixture 700 µl MPI-2 cocktail is added dropwise with stirring. The sol is stirred for 1 hour, then is allowed to stand for 18 hours. Finally 100 µl of dimethyl-dimethoxysilane is added thereto, is shaken together, and after 30 minutes of standing 1 ml of ethanol is added. 100 micrometer thick sensor membranes are prepared onto glass supports in advance.

After one additional day of drying, spectrophotometrically studying of the pH dependence of the sensors, the calibration curve according to FIG. 3 can be obtained. The horizontal axis x according to the calibration curve of FIG. 3 demonstrates the pH value, its vertical axis y demonstrates the value of change in the absorbance (ΔAbsorbance). It can be noted that the sensor, similarly to the sensor shown in FIG. 2, is suitable for measuring pH in the pH=2 to 10 range. It is considered to be a significant difference, however, that the change in the signal measurable as a function of the pH is almost linear. This considerably facilitates the precise determination of the pH during the measurements.

Example 8: The Chemical Stabilization of the Indicator on Cellulose Surface

In case of a cellulose-based support, reacting the polymer according to Formula (I') with a diisocyanate derivative [such as hexamethylene diisocyanate or 4,4'-methylene bis (phenyl isocyanate)] in 1:1 proportion, a polymer according to Formula (I) is obtained, wherein $L_2$ stands for an isocyanato group. The product is not separated from the mixture, it is rather directly applied to the cellulose support, to the —OH groups of which the polymer according to Formula (I) can be attached via its isocyanato group covalently—by forming of an urethane bond.

Example 9: The Chemical Stabilization of the Indicator on the Surface of a Support Containing Amino Group In case of supports containing primary or secondary amino group [such as aminoethyl-cellulose, polyurethane, poly(ethylene-imine)] the process according to Example 8 is followed. In this case a carbamide bond is formed during the reaction.

Example 10: An Alternative Stabilization of the Indicator

The chemical stabilization described in the above examples can be accomplished also in such a way that first the support is treated with excess isocyanate derivative, then it is immersed in the non-aqueous solution of the polymer according to Formula (I') without separation, or this solution is spread on the surface of the support. Thus a supported polymer identical with those above is obtained.

What is claimed is:

1. A method for measuring pH, said method comprising applying a sample whose pH is to be measured to an optical indicator, wherein the optical indicator comprises a support, and one or more p-nitro-phenyl/formaldehyde condensed polymer according to Formula (I) in the state of being stabilized to said support

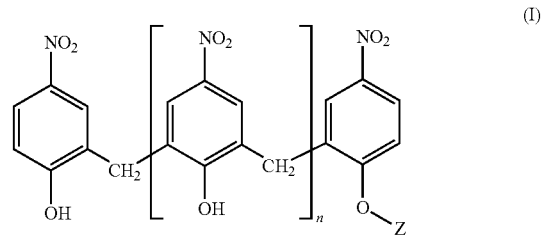

(I)

wherein n has the value of 1 to 20, and Z stands for H or a binding group.

2. The method as claimed in claim 1, wherein the pH to be measured is in the range of 1.8 to 10.

3. The method as claimed in claim 1, wherein the p-nitro-phenyl/formaldehyde condensed polymer according to Formula (I) is stabilized to the support by a physical bond.

4. The method as claimed in claim 1, wherein the p-nitro-phenyl/formaldehyde condensed polymer according to Formula (I) is stabilized to the support by a chemical bond.

5. The method as claimed in claim 1, wherein in Formula (I) Z stands for a group according to the Formula $L_1'$-R-$L_2$, wherein $L_1'$ stands for a) 2-hydroxyethane 1,2-diyl group

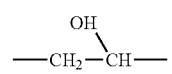

b) 6-hydroxy-phenyl-1,3-diyl group

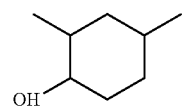

c) thiocarbonylamino group

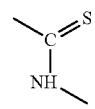

d) carbonylamino group

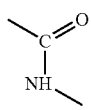

e) carbonyl group

R stands for a direct bond or $C_1$-$C_{20}$ saturated, unsaturated or aromatic, straight or branched or cyclic, bifunctional hydrocarbon group, $L_2$ stands for a) alkoxy-silanyl group

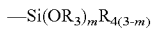

wherein m has a value of 1 to 3, $R_3$ stands for hydrogen or a $C_1$-$C_6$ alkyl group, $R_4$ stands for $C_1$-$C_{20}$ saturated, unsaturated or aromatic, straight or branched or cyclic, monofunctional hydrocarbon group or a perfluorinated vagy aminated derivative thereof, b) isothiocyanato group

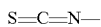

c) isocyanato group

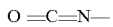

d) acid halogenide group

wherein X stands for halogen atom e) ester group

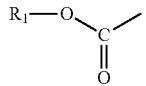

wherein $R_1$ stands for $C_1$-$C_6$ alkyl group f) carboxyl group

g) mercapto group

6. The method as claimed in claim 1, wherein the support is a silica nanopearl, the diameter of which is 0.01-2 μm.

7. The method as claimed in claim 1, wherein the support is a silicon nanopearl, having a diameter of 0.01 to 2 μm.

* * * * *